US00PP30083P2

(12) United States Plant Patent
Eggleton

(10) Patent No.: US PP30,083 P2
(45) Date of Patent: Jan. 8, 2019

(54) ***LAVANDULA* PLANT NAMED 'IBPRU41016'**

(50) Latin Name: *Lavandula penduculata*
Varietal Denomination: IBPRU41016

(71) Applicant: Plant Growers Australia, Wonga Park (AU)

(72) Inventor: Steven Eggleton, Wonga Park (AU)

(73) Assignee: Plant Growers Australia, Wonga Park (AU)

( * ) Notice: Subject to any disclaimer, the term of this patent is extended or adjusted under 35 U.S.C. 154(b) by 0 days.

(21) Appl. No.: 15/732,578

(22) Filed: Nov. 29, 2017

(30) Foreign Application Priority Data

Mar. 1, 2017 (QZ) ..... PBR 2017/0621

(51) Int. Cl.
*A01H 5/02* (2018.01)

(52) U.S. Cl.
USPC ..... Plt./445

(58) Field of Classification Search
USPC ..... Plt./445
See application file for complete search history.

*Primary Examiner* — Annette H Para
(74) *Attorney, Agent, or Firm* — Samuel R. McCoy, Jr.

(57) ABSTRACT

'IBPRU41016' is a new and distinctive variety of *Lavandula* plant which is characterized by a compact growth habit, an abundance of dark violet-blue flowers borne on terminal spike inflorescences held slightly above the foliage, and very large purple sterile bracts with heavily undulating margins at the apex of each inflorescence. The new variety propagates successfully by stem cuttings and has shown to be uniform and stable in the resulting generations from asexual propagation.

3 Drawing Sheets

Latin name of the genus and species: The Latin name of the genus and species of the novel variety disclosed herein is *Lavandula penduculata.*

Variety denomination: The inventive variety of *Lavandula* disclosed herein has been given the variety denomination 'IBPRU41016'.

CROSS REFERENCE TO RELATED APPLICATIONS

This application claims priority to the Community Plant Variety Rights application number 2017/0621, filed Mar. 1, 2017, which is herein incorporated by reference.

BACKGROUND OF THE INVENTION

Parentage: 'IBPRU41016' is the result of a controlled cross-pollination breeding program carried out by the inventor at a commercial nursery in Wonga Park, Victoria, Australia. The objective of the breeding program was to develop a cultivar or cultivars with a compact growth habit, shorter inflorescences and large infertile bracts of various colors. In November of 2013, the inventor performed a controlled cross-pollination of the seed parent, *Lavandula* 'Blueberry Ruffles' (U.S. Plant Pat. No. 18,305), and *Lavandula* 'Violet Lace' (U.S. Plant Pat. No. 18,254), the pollen parent. Seed U.S. Plant Pat. No. 18,254), the pollen parent. Seed from said cross was harvested, then germinated in February of 2014, and the resulting seedlings were grown to a mature size in a 140 mm nursery container in order to evaluate for a desirable combination of commercial characteristics such as compact plant size, large inflorescence and unique flower and bract color. In October of 2014, one candidate plant was observed to exhibit a unique combination of traits and, after confirmation of the distinctness and stability of the characteristics first observed, the inventor selected the new *Lavandula* cultivar, 'IBPRU41016', for commercial introduction.

Asexual Reproduction: Asexual reproduction of 'IBPRU41016' was first accomplished in February of 2015 by rooting softwood stem cuttings at a commercial nursery in Wonga Park, Victoria, Australia. Four successive generations have shown that the unique features of the instant cultivar are stable and reproduce true to type.

SUMMARY OF THE INVENTION

The cultivar 'IBPRU41016' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Lavandula* cultivar, 'IBPRU41016'.

1. *Lavandula* 'IBPRU41016' exhibits a compact growth habit; and
2. *Lavandula* 'IBPRU41016' exhibits dark green foliage with dense tomentose pubescence and undulating margins; and
3. *Lavandula* 'IBPRU41016' exhibits an abundance of dark violet-blue flowers borne on terminal spike inflorescences held slightly above the foliage; and
4. *Lavandula* 'IBPRU41016' exhibits very large purple sterile bracts with heavily undulating margins at the apex of each inflorescence.

BOTANICAL DESCRIPTION OF THE PLANT

Figure 1:
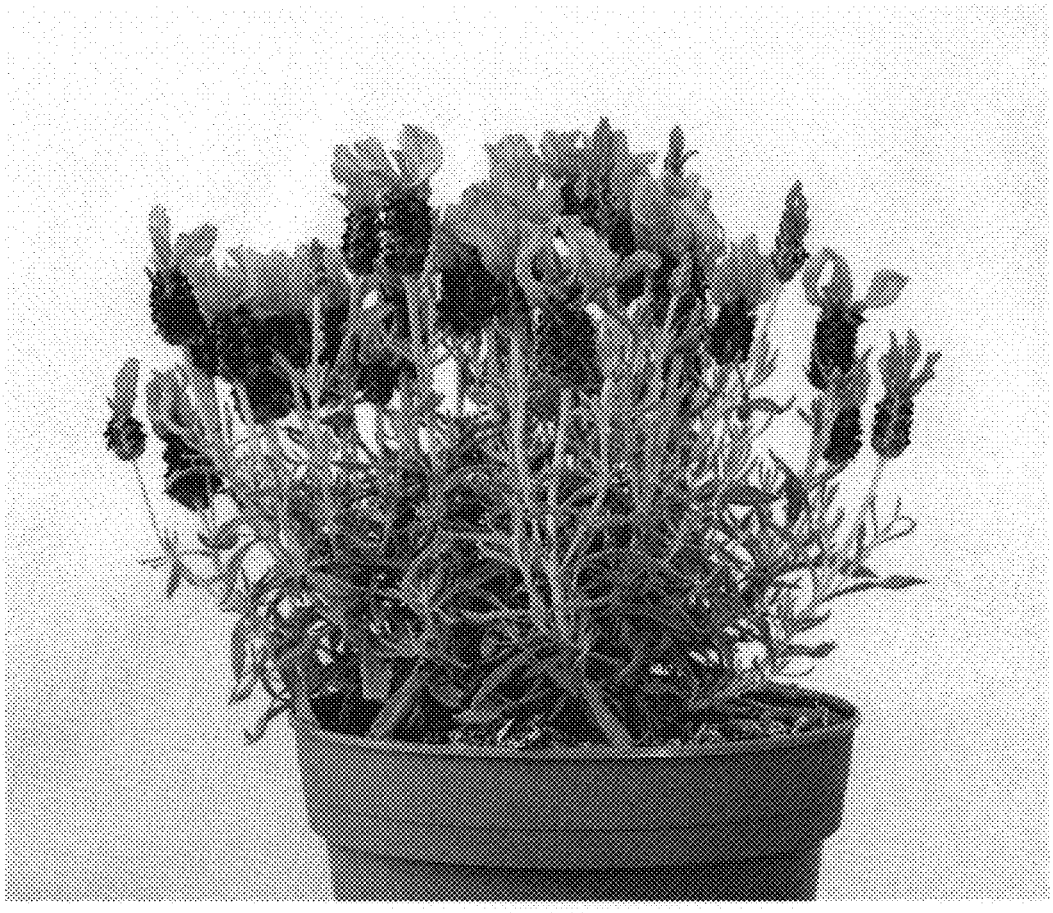
FIG. 1 shows, as nearly true as it is reasonably possible to make the same in color illustrations of this type, an exemplary 'IBPRU41016' plant at approximately 30 months old, potted into a 13 cm nursery pot, grown outdoors in Oudenaarde, Belgium.
Figure 2:
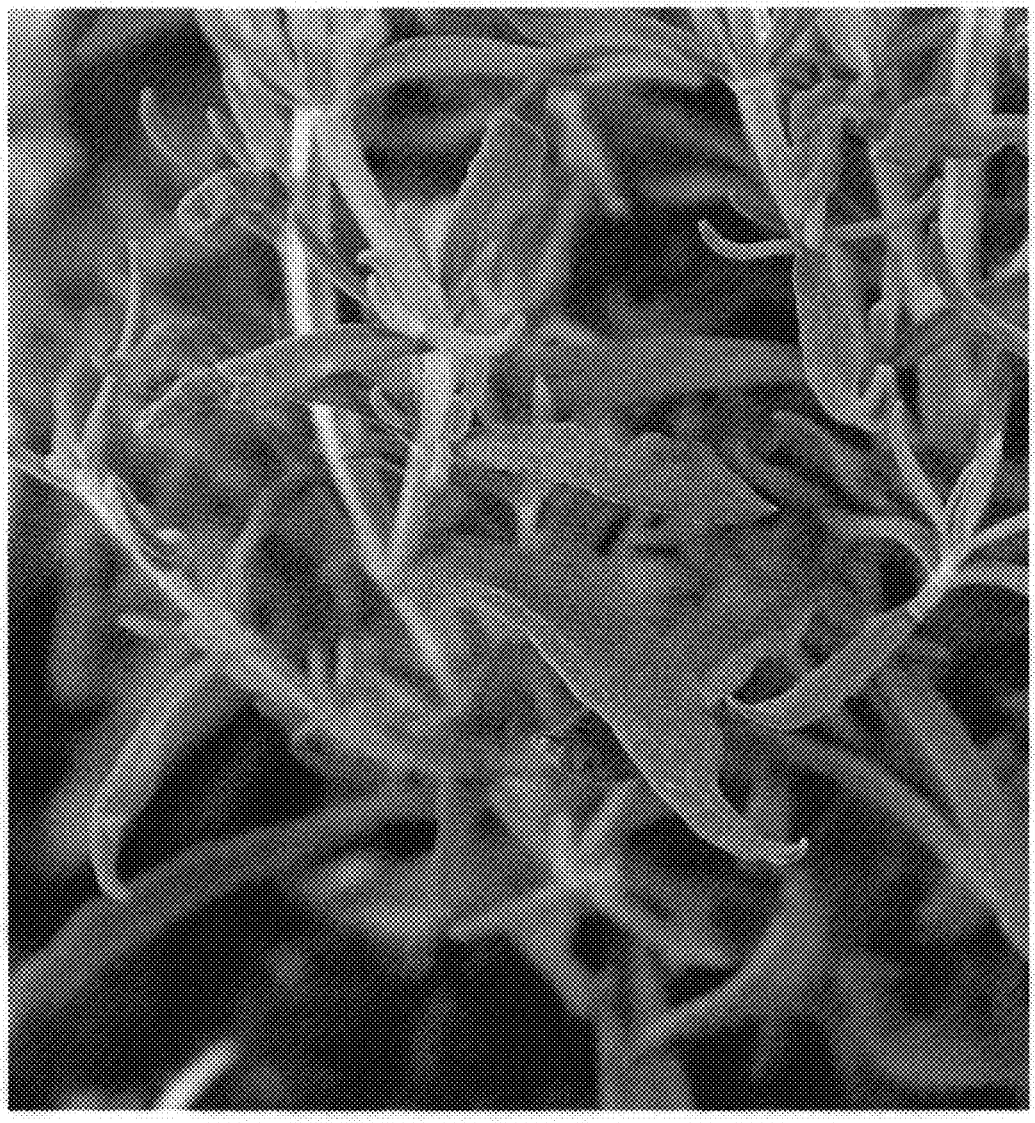
FIG. 2 shows, as nearly true as it is reasonably possible to make the same in color illustrations of this type, the typical foliage of the plant in FIG. 1.
Figure 3:
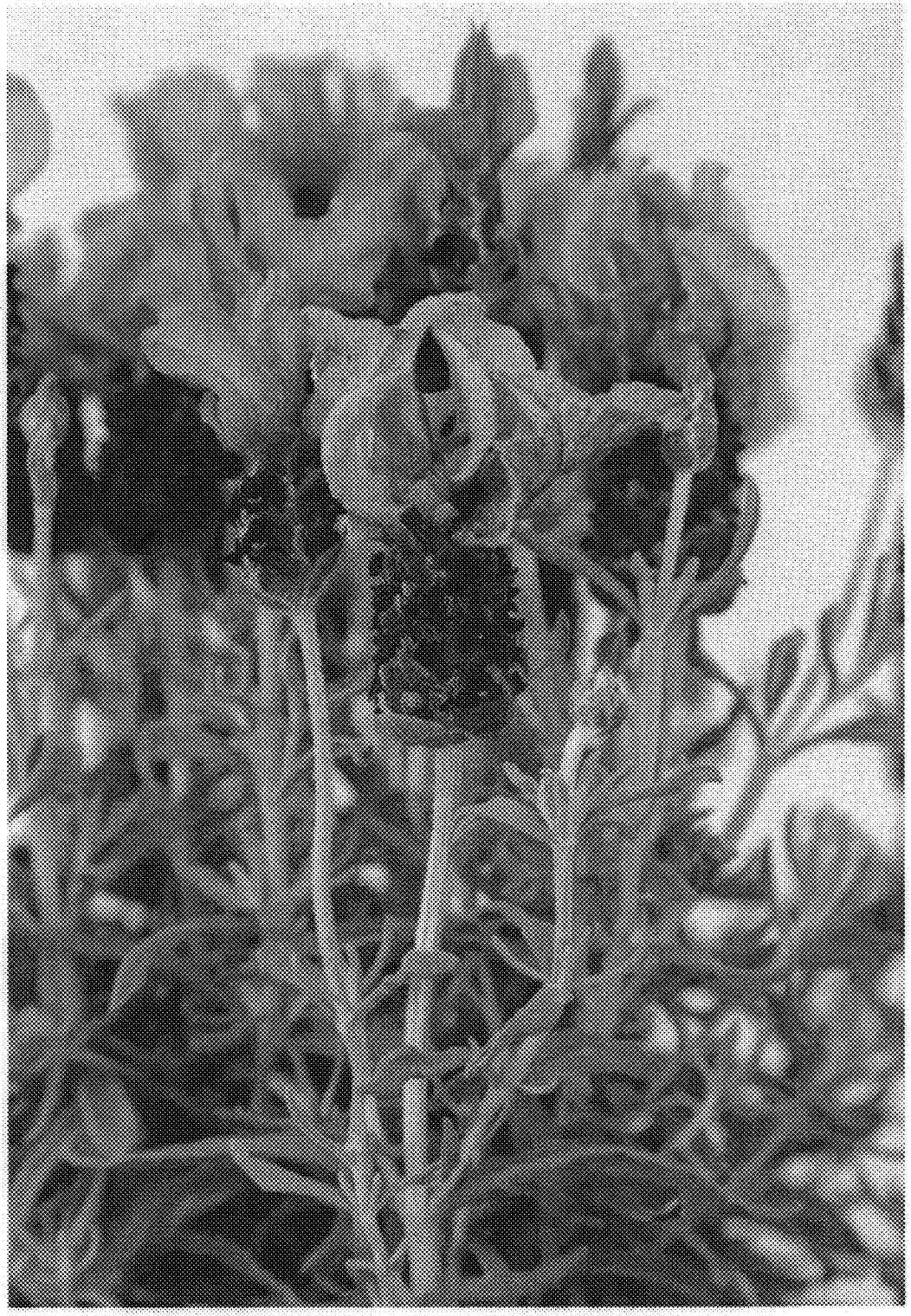
FIG. 3 shows, as nearly true as it is reasonably possible to make the same in color illustrations of this type, the typical inflorescence of the plant in FIG. 1.

The following is a detailed botanical description of a new and distinct variety of *Lavandula* known as 'IBPRU41016', based upon observations of 30 month old field-grown plants in 13 cm nursery containers, produced in Oudenaarde, Belgium. Plants were produced in full sun using conventional production protocols for *Lavandula* plants which consisted of regular overhead irrigation, slow-release fertilizer applications as needed, and preventative fungicide applications on a monthly basis. Observation data was recorded in June of 2017.

Those skilled in the art will appreciate that certain characteristics will vary with older or, conversely, with younger plants. 'IBPRU41016' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 edition.

A botanical description of 'IBPRU41016' and comparisons with the parent plants are provided below.

General plant description:

*Growth habit*.—A broad, spreading to upright perennial subshrub.

*Plant form*.—Flattened globular.

*Height*.—12.8 cm to the top of the foliar plane; 18.1 cm to the top of the floral plane.

*Spread*.—22.6 cm.

*Plant vigor*.—Low.

*Growth rate*.—Low to moderate.

*Propagation*.—Softwood stem cuttings; rooting is initiated in approximately 10 days when grown at an ambient average temperature of 21 degrees Celsius.

*Pest resistance and susceptibility*.—Not any more or less tolerant or susceptible to pests or diseases known to effect *Lavandula*.

*Environmental tolerances*.—Adapt to, at least, USDA Zones 7 to 10 and temperatures to at least 40 degrees Celsius; moderate tolerance to rain; high tolerance to wind.

Root system: Dense fibrous root system; relatively shallow; color of juvenile roots is nearest to yellow-white, RHS 158B; older roots are greyed-orange, RHS 163C.

Stem:

*Branching habit*.—Basally branching main stems; freely branching with lateral branches. Stems and branches are strongly aromatic, typical of *Lavandula*. Pinching isn't required but will improve branching.

*Number of primary (main) stems per plant*.—10.

*Number of secondary (lateral) branches per plant*.—40.

*Lateral branch length*.—6.8 cm.

*Lateral branch diameter*.—0.2 cm.

*Lateral branch internode length*.—0.9 cm.

*Appearance and shape*.—Quadrangular.

*Aspect of main stems*.—35 degrees from vertical, on average; varying between 0 and 70 degrees.

*Aspect of lateral branches*.—25 degrees to main stems.

*Luster*.—Matte, due to the dense woolly pubescence.

*Strength*.—Moderately strong.

*Color, juvenile*.—Yellow-green, nearest RHS 144C.

*Color, mature*.—Yellow-green, nearest to RHS 151D.

*Color of oldest stems*.—Greyed-brown, nearest to RHS N199A.

*Color at internodes*.—Yellow-green, nearest to in between RHS 145A and N145B.

*Pubescence*.—Tomentose; average length of hairs is 0.03 cm and colored translucent white, nearest to RHS 155C.

Foliage:

*Arrangement*.—Opposite.

*Attachment*.—Sessile.

*Division*.—Simple.

*Attitude*.—Upward; apex occasionally curled upward or downward.

*Quantity*.—Average of 8 leaves per lateral branch.

*Fragrance*.—Strongly aromatic, typical of *Lavandula*.

*Lamina*.—Dimensions — 3.8 cm long and 0.7 cm wide, on average. Shape — Oblanceolate to narrow oblanceolate. Aspect — Slightly twisted; slightly to moderately revolute. Apex — Acute. Base — Cuneate. Margin — Entire; moderately undulated. Apex — Acute. Base — Cuneate. Margin — Entire; moderately undulated. Pubescence of adaxial surface — Tomentose; average length of hairs is 0.02 cm and colored green-white, nearest to RHS 157D but lighter. Pubescence of abaxial surface — Tomentose; average length of hairs is 0.02 cm and colored green-white, nearest to RHS 157D but lighter. Luster of adaxial surface — Matte. Luster of abaxial surface — Matte. Color — Juvenile foliage, adaxial surface — Green, nearest to RHS 137B. Juvenile foliage, abaxial surface — Green, nearest to in between RHS 137B to 137C. Mature foliage, adaxial surface — Green, nearest to RHS 137B. Mature foliage, abaxial surface — Green, nearest to RHS 137C. Venation — Pattern — Pinnate. Venation color, adaxial surface — Yellow-green, nearest to RHS 148B. Venation color, abaxial surface — Green, nearest to RHS 138B.

Inflorescence:

*Type*.—Terminal spike.

*Natural flowering season*.—Late spring through late summer in Victoria, Australia.

*Time to flower*.—Approximately 13 weeks.

*Dimensions*.—4.4 cm high, not including peduncle, and 1.6 cm in diameter; the sterile bracts at the apex of each inflorescence have an average spread of 3.2 cm.

*Abundance of inflorescence*.—Very abundant.

*Quantity of open flowers and buds per inflorescence*.—400.

*Quantity of open flowers per plant*.—Approximately 850.

*Quantity of buds per plants*.—Approximately 1,150.

*Attitude*.—Upright.

*Peduncles*.—Length — Average of 4.0 cm. Diameter — Average of 0.15 cm. Attitude — Upright; 0 degrees to the lateral branches. Strength — Strong. Texture — Tomentose; average length of hairs is 0.03 cm and colored translucent white, nearest to RHS 155C. Luster — Matte. Color — Yellow-green, nearest to 150B.

Flower buds:

*Shape*.—Elliptic.

*Length*.—Average of 0.5 cm.

*Diameter*.—Average of 0.175 cm.

*Texture*.—Tomentose; average length of hairs is 0.03 cm and colored white, nearest to RHS NN155D.

*Luster*.—Matte.

*Color*.—Yellow-green, nearest to RHS 144A, upper half of the bud is heavily suffused with greyed-purple, nearest to RHS N186A; apex where immature petals are exposed is violet-blue, nearest to RHS 92A.

Flower:

*Flowering habit*.—Freely flowering.

*Form*.—Salverform; petals fused into one upper lip which is split into two identical petal lobes, and one lower lip which is split into three identical petal lobes.

*Flower vertical height*.—0.5 cm.

*Flower diameter*.—0.45 cm.

*Flower length*.—0.7 cm.

*Floral throat diameter*.—0.1 cm.

*Floral throat texture*.—Glabrous; smooth.

*Diameter of floral tube*.—0.1 cm.

*Length of floral tube*.—0.5 cm.

*Floral tube texture, outer and inner surfaces*.—Distal one-third portion is moderately covered with a very short pubescence with an average length of 0.3 cm and colored white, nearest to RHS NN155D; the proximal two-thirds portion is glabrous and smooth.

*Aspect*.—Flowers are outward facing.

*Fragrance*.—Non-fragrant.

*Lastingness*.—Approximately 4 weeks.

*Persistent*.—Self-cleaning.

*Pedicels*.—None; flowers are sessile.

*Petals*.—Quantity of Petals — 2. Arrangement — Labiate; one upper lip and one lower lip; proximal 72.5% of the petals are fused. Shape of petal lobes — Upper and lower petal lobes are spatulate. Dimensions, upper petal lobes — 0.6 cm long and 0.15 cm wide. Dimensions, free portion of the lower petal — 0.6 cm long and 0.15 cm wide. Apex — Both the upper and lower petal lobes are obtuse. Base — Fused into a tube. Margin — All petal lobs with entire margins which are moderately undulated. Aspect — Slightly curled upward at the apex of the lobes. Texture and luster of upper surface — Velvety; matte. Texture and luster of lower surface — Moderately velvety; slightly glossy. Petal color when opening, upper surface — Violet-blue, nearest to RHS N92A. Petal color when opening, lower surface — Violet-blue, nearest to RHS N92A. Petal color when fully opened, upper surface — Violet-blue, nearest to RHS N92A. Petal color when fully opened, lower surface — Violet-blue, nearest to RHS N92A. Petal venation — No venation is visible. Floral throat color — Violet, nearest to in between RHS 83B and 83C. Floral throat venation color — No venation is visible. Corolla tube color, when fully opened — Violet, nearest to in between RHS 83B and 83C, and fading white towards the base, RHS N155D. Floral tube venation color — No venation is visible.

*Calyx*.—Shape — Campanulate. Length — 0.6 cm. Diameter — 0.2 cm. Sepals — Length — 0.6 cm. Width — 0.075 cm. Arrangement — Fused into a campanulate shape; proximal 83.5% is fused. Quantity — 5. Shape — Linear; fused into a campanulate shape. Apex — Acute. Base — Basally fused; only the distal 16.5 percent is free. Sepal lobe margin — Entire; not undulated. Texture and luster, upper surface — Glabrous, smooth; matte. Texture and luster, lower surface — Tomentose; average length of hairs is 0.03 cm and colored white, nearest to RHS NN155D; matte. Color when opening, upper surface — Yellow-green, nearest to RHS 145B, and striped darker, nearest to RHS 146B. Color when opening, lower surface — Yellow-green, nearest to RHS 144A; distal half is heavily suffused with greyed-purple, nearest the RHS N186A. Color when fully opened, upper surface — Yellow-green, nearest to RHS 145B, and striped green, nearest to in between RHS 143A and 143B. Color when fully opened, lower surface — Yellow-green, nearest to RHS 145B, and striped green, nearest to in between RHS 143A and 143B.

*Bract*.—Quantity — One fertile bract present at the base of each group of 5 individual flowers; 7 sterile bracts at the apex of each inflorescence. Fertile bract — Shape — Broad rhomboidal. Dimensions — Average of 0.75 cm long and 0.65 cm wide. Apex — Aristate. Base — Cuneate. Margins — Entire; not undulated. Texture and luster, upper surface — Glabrous; matte. Texture and luster, lower surface — Moderately tomentose; average length of hairs is 0.03 cm and colored white, nearest to RHS NN155D; matte. Color, upper surface — Yellow-green, nearest to RHS 145D; apex is suffused with greyed-red, nearest to RHS 181D. Color, lower surface — Yellow-green, nearest to RHS 145D; upper half is suffused with greyed-purple, nearest to RHS 185D. Venation color, upper surface — Green, nearest to in between RHS 137B and 137C. Venation color, lower surface — Green, nearest to RHS 143A. Sterile bracts — Shape — Obovate to narrow obovate. Dimensions — Average of 2.4 cm long and 1.2 cm wide. Apex — Obtuse. Base — Narrow cuneate. Margins — Entire; strongly undulated. Texture and luster, upper surface — Slightly to moderately tomentose; average length of hairs is 0.02 cm and colored white, nearest to RHS NN155D; matte. Texture and luster, lower surface — Slightly to moderately tomentose; average length of hairs is 0.02 cm and colored white, nearest to RHS NN155D; matte. Color, upper surface — Purple-violet, nearest to in between RHS N82A and N82B. Color, lower surface — Purple-violet, nearest to in between RHS N82A and N82B. Venation color, upper surface — Main vein is purple, nearest to in between RHS N77C and N77D. Venation color, lower surface — Main vein is purple, nearest to RHS N77B.

Reproductive organs:

*Stamens*.—Quantity — 4. Anthers — Attachment — Dorsifixed. Shape — Short kidney-shaped. Dimensions — Approximately 0.075 cm long and 0.075 cm wide. Color — Greyed-purple, nearest to RHS N187A. Filaments — Length — 0.1 cm, on average. Color — Violet, nearest to RHS 83A. Pollen, amount — Moderately abundant. Pollen color — Yellow-orange, nearest to RHS 15A.

*Pistil*.—Quantity — 1. Length — 0.4 cm. Style — Length — 0.35 cm. Color — Greyed-white, nearest to RHS 156D. Stigma — Shape — Club-shaped. Length — 0.05 cm. Diameter — 0.05 cm. Color — Greyed-purple, nearest to RHS N187A. Ovary Color — Yellow-green, nearest to RHS 146A.

Seed and fruit: No fruit or seeds have been detected to date.

Comparisons With the Parent Plants and Most Similar Commercial Variety

Plants of the new cultivar 'IBPRU41016' differ from its seed parent, which is also the most similar commercial variety, *Lavandula* 'Blueberry Ruffles' (U.S. Plant Pat. No. 18,305), by the characteristics described in Chart 1.

CHART 1

| Characteristic | 'IBPRU41016' | 'Blueberry Ruffles' |
|---|---|---|
| Plant height. | Shorter than 'Blueberry Ruffles'. | Slightly taller than 'IBPRU41016'. |
| Peduncle length. | Shorter than 'Blueberry Ruffles'. | Longer than 'IBPRU41016'. |
| General coloration of sterile bracts. | Medium to dark purple. | Light mauve purple. |

Plants of the new cultivar 'IBPRU41016' differ from its pollen parent, *Lavandula* 'Violet Lace' (U.S. Plant Pat. No. 18,254), by the characteristics described in Chart 2.

CHART 2

| Characteristic | 'IBPRU41016' | 'Violet Lace' |
|---|---|---|
| Growth habit. | More compact than 'Violet Lace'. | Less compact than 'IBPRU41016'. |
| Plant height. | Shorter than 'Violet Lace'. | Taller than 'IBPRU41016'. |
| Peduncle length. | Shorter than 'Violet Lace'. | Longer than 'IBPRU41016'. |

That which is claimed is:

1. A new and distinct variety of *Lavandula* plant named 'IBPRU41016', substantially as described and illustrated herein.

* * * * *